United States Patent
Kanazawa

(10) Patent No.: US 7,663,365 B2
(45) Date of Patent: Feb. 16, 2010

(54) MAGNETIC RESONANCE IMAGING APPARATUS AND ANALYSIS METHOD FOR FAT SUPPRESSION EFFECT IN MAGNETIC RESONANCE IMAGING APPARATUS

(75) Inventor: Hitoshi Kanazawa, Utsunomiya (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 12/236,753

(22) Filed: Sep. 24, 2008

(65) Prior Publication Data

US 2009/0085566 A1  Apr. 2, 2009

(30) Foreign Application Priority Data

Sep. 28, 2007  (JP)  ............................. 2007-255704

(51) Int. Cl.
G01V 3/00 (2006.01)
A61B 5/055 (2006.01)

(52) U.S. Cl. .................. 324/309; 324/310; 324/312; 324/314; 324/318; 324/307; 600/410; 600/411; 600/425

(58) Field of Classification Search ......... 324/300–322; 600/407–435; 382/128–131
See application file for complete search history.

(56) References Cited

U.S. PATENT DOCUMENTS

| | | | | |
|---|---|---|---|---|
| 4,585,993 A | * | 4/1986 | Bottomley | .................. 324/309 |
| 5,304,931 A | * | 4/1994 | Flamig et al. | ................ 324/309 |
| 5,578,921 A | * | 11/1996 | Morrell | ....................... 324/307 |
| 6,448,773 B1 | | 9/2002 | Zhang | ......................... 324/309 |
| 6,933,720 B2 | * | 8/2005 | Zhang | ......................... 324/309 |
| 7,253,620 B1 | * | 8/2007 | Derbyshire et al. | ......... 324/307 |
| 7,420,368 B2 | * | 9/2008 | Miyazaki | .................... 324/307 |
| 7,518,364 B1 | * | 4/2009 | Cukur | ........................ 324/309 |
| 2003/0109781 A1 | * | 6/2003 | Zhang | ......................... 600/410 |
| 2007/0225591 A1 | * | 9/2007 | Derbyshire et al. | ......... 600/410 |
| 2007/0229070 A1 | * | 10/2007 | Miyazaki | .................... 324/307 |
| 2009/0072826 A1 | * | 3/2009 | Hargreaves et al. | ......... 324/309 |
| 2009/0085566 A1 | * | 4/2009 | Kanazawa | .................. 324/309 |
| 2009/0091324 A1 | * | 4/2009 | Sugiura | ...................... 324/309 |

FOREIGN PATENT DOCUMENTS

JP  3-51172  8/1991

OTHER PUBLICATIONS

Haase, A. et al., $^1$H NMR Chemical Shift Selective (CHESS) Imaging, Phys. Med. Biol., vol. 30, No. 4, pp. 341-344, (1985).

* cited by examiner

*Primary Examiner*—Brij B. Shrivastav
*Assistant Examiner*—Tiffany A Fetzner
(74) *Attorney, Agent, or Firm*—Nixon & Vanderhye PC

(57) ABSTRACT

A magnetic resonance imaging apparatus includes an imaging unit which performs imaging more than once with respect to an imaging target while changing a central frequency of a fat suppression pulse, a generation unit which generates a plurality of images based on magnetic resonance signals obtained by imaging performed more than once, and a calculation unit which calculates factor information of spatial inhomogeneity of a fat suppression effect based on the plurality of images.

10 Claims, 10 Drawing Sheets

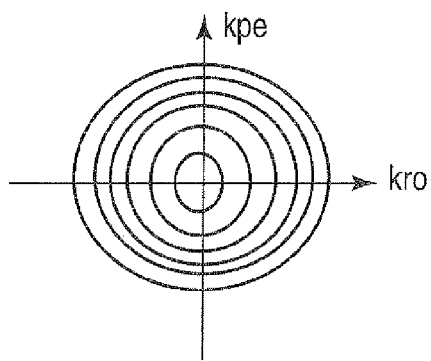 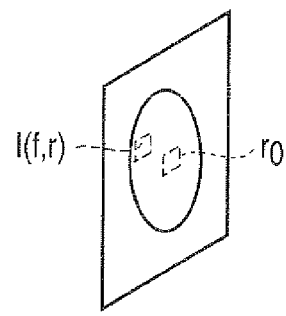
FIG. 4　　　　　　　FIG. 5
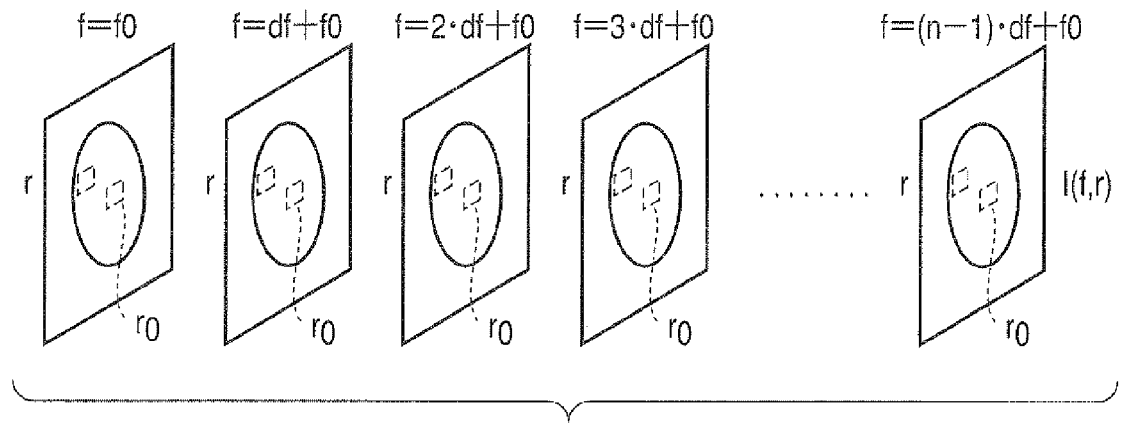
FIG. 6
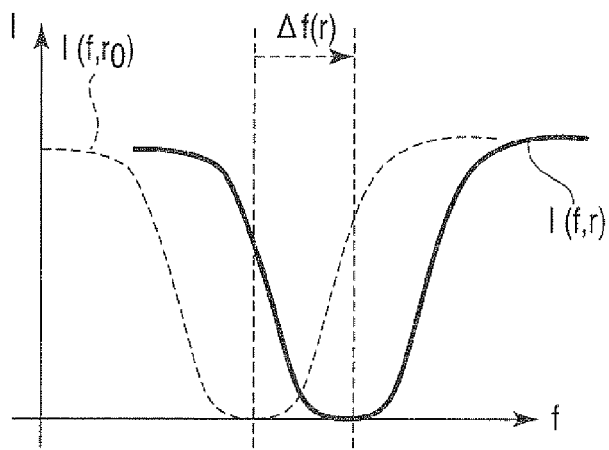
FIG. 7

MAGNETIC RESONANCE IMAGING APPARATUS AND ANALYSIS METHOD FOR FAT SUPPRESSION EFFECT IN MAGNETIC RESONANCE IMAGING APPARATUS

CROSS-REFERENCE TO RELATED APPLICATIONS

This application is based upon and claims the benefit of priority from prior Japanese Patent Application No. 2007-255704, filed Sep. 28, 2007, the entire contents of which are incorporated herein by reference.

BACKGROUND OF THE INVENTION

1. Field of the Invention

The present invention relates to a magnetic resonance imaging apparatus that applies a fat suppression pulse to achieve suppression of a fat signal and an analysis method for a fat suppression effect in this magnetic resonance imaging apparatus.

2. Description of the Related Art

As a fat suppression method in magnetic resonance imaging, a chemical shift selective (CHESS) method or a spatial-spectral excitation pulse method is known.

In any of these fat suppression methods, spatial inhomogeneity of a fat suppression effect occurs. As a method of improving spatial inhomogeneity of the fat suppression effect, there is so-called current shimming. In the current shimming, a spatial distribution of a magnetic field is measured before imaging. Further, at the time of imaging, a temporally fixed correction current is flowed through a gradient magnetic field coil or a magnetic field correction coil while considering the spatial distribution of the magnetic field measured before imaging, thereby correcting the spatial inhomogeneity of the fat suppression effect.

A relevant technology is known from, e.g., JP-A H03-51172 (KOKOKU).

In the above-explained current shimming, a gradient magnetic field waveform in a pulse sequence required to measure a spatial distribution of a magnetic field is different from a gradient magnetic field waveform in a pulse sequence that also adopts fat suppression. Therefore, a eddy magnetic field generated due to a gradient magnetic field differs depending on measurement of a spatial distribution of a static magnetic field and imaging involving fat suppression. That is, a spatial distribution of a magnetic field measured before imaging is different from a spatial distribution of a magnetic field at a moment where a fat suppression pulse or a water excitation pulse is applied for fat suppression. Therefore, a correction current set based on a spatial distribution of a magnetic field measured before imaging cannot sufficiently eliminate spatial inhomogeneity of a fat suppression effect in some cases. Furthermore, since spatial inhomogeneity of the fat suppression effect based on a static magnetic field distribution is corrected, spatial inhomogeneity of the fat suppression effected caused due to spatial inhomogeneity of a radio-frequency magnetic field cannot be corrected. That is, the conventional technology cannot prevent spatial inhomogeneity of the fat suppression effect involved by spatial inhomogeneity of a radio-frequency magnetic field or a eddy magnetic field from affecting an image.

Meanwhile, spatial inhomogeneity of a radio-frequency magnetic field or a eddy magnetic field varies depending on each apparatus due to, e.g., malfunction of the apparatus, a manufacturing error of a gradient magnetic field coil or an RF coil, or good or poor results of apparatus adjustment in an installing operation or a maintenance operation. Therefore, when spatial inhomogeneity of the fat suppression effect prominently appears in an image taken by a given apparatus, great labor is required to confirm whether a phenomenon can be improved while sequentially taking countermeasures from which effects are likely to be expected (adjustment or component replacement) in regard to each of the above-explained factors.

BRIEF SUMMARY OF THE INVENTION

Under the circumstances, efficiently improving spatial inhomogeneity of the fat suppression effect has been demanded.

According to a first aspect of the present invention, there is provided a magnetic resonance imaging apparatus comprising: an imaging unit which performs imaging more than once with respect to an imaging target while changing a central frequency of a fat suppression pulse; a generation unit which generates a plurality of images based on magnetic resonance signals obtained by imaging performed more than once; and a calculation unit which calculates factor information of spatial inhomogeneity of a fat suppression effect based on the plurality of images.

According to a second aspect of the present invention, there is provided an analysts method for a fat suppression effect in magnetic resonance imaging, comprising: performing imaging more than once with respect to an imaging target while changing a central frequency of a fat suppression pulse; generating a plurality of images based on MR signals obtained by imaging performed more than once; and calculating factor information of spatial inhomogeneity of the fat suppression effect based on the plurality of images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description or the embodiments given below, serve to explain the principles of the invention.

FIG. 4 is a view showing an example of a k-space;

FIG. 5 is a view showing an example of a reconstructed image;

FIG. 6 is a view showing a conceptual illustration of images created by processing depicted in FIG. 2;

FIG. 7 is a view showing an example of frequency spectrums at the center of a magnetic field and any other position;

DETAILED DESCRIPTION OF THE INVENTION

An embodiment according to the present invention will now be explained hereinafter with reference to the accompanying drawings.

Figure 1:
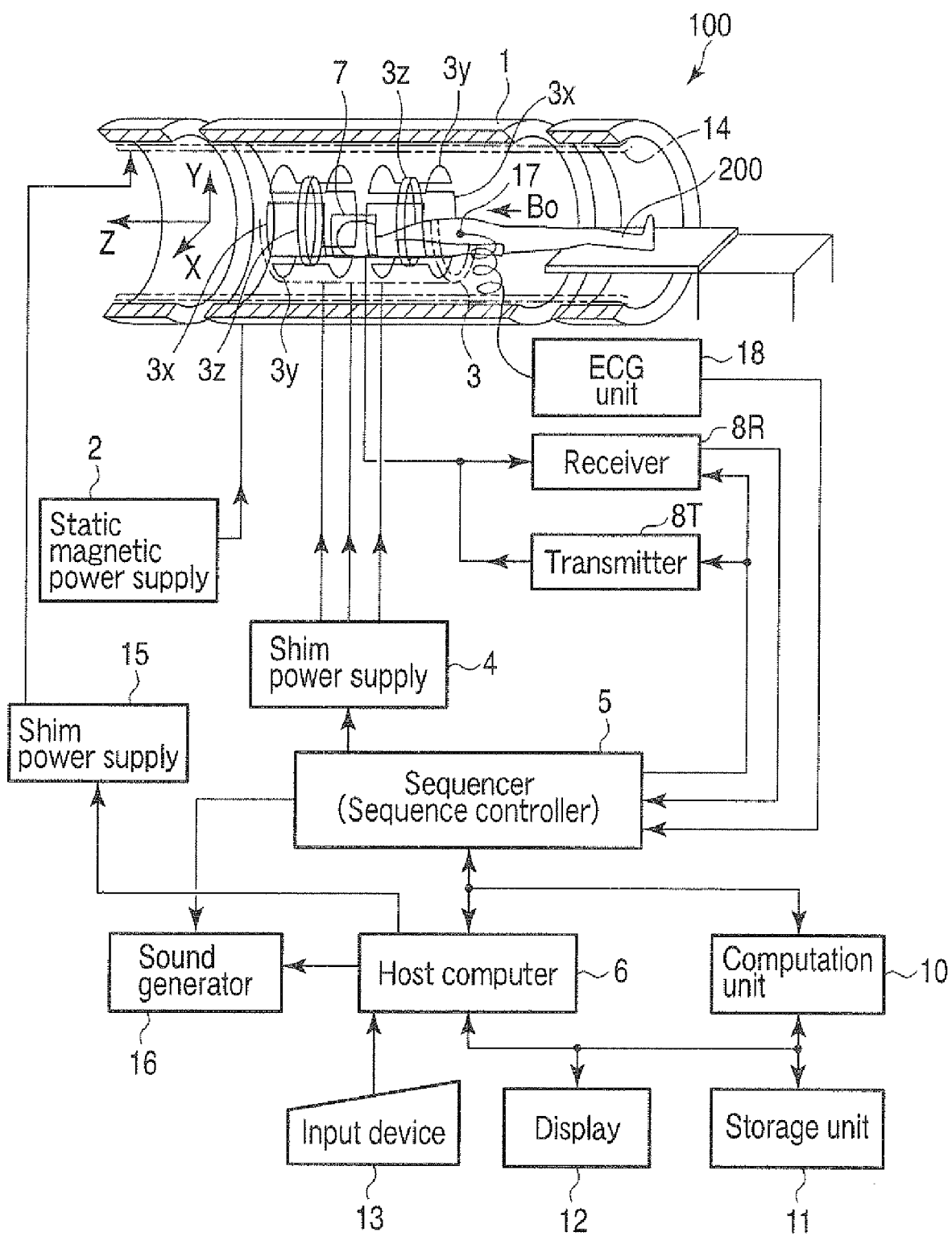
FIG. 1 is a view showing a structure of a magnetic resonance imaging apparatus according to an embodiment of the present invention.

FIG. 1 is a view showing a structure of a magnetic resonance imaging apparatus (which will be referred to as an MRI apparatus hereinafter) 100 according to this embodiment.

This MRI apparatus 100 includes a bed unit on which a subject 200 is mounted, a static-magnetic-field generating unit that generates a static magnetic field, a gradient-magnetic-field generating unit that adds position information to the static magnetic field, a transmitting/receiving unit that transmits/receives a radio-frequency signal, and a control/computation unit that performs control over the entire system and image reconstruction. Further, the MRI apparatus 100 has a magnet 1, a static magnetic power supply 2, a gradient coil unit 3, a gradient power supply 4, a sequencer (a sequence controller) 5, a host computer 6, an RF coil unit 7, a transmitter 8T, a receiver 6R, a computation unit 10, a storage unit 11, a display device 12, an input device 13, a shim coil 14, and a shim coil power supply 15 as constituent elements of the respective units. Furthermore, the MRI apparatus 100 includes an electrocardiograph unit that measures an ECG signal as a signal indicative of a cardiac time phase of the subject 200 and a breadth-holding instruction unit that instructs the subject 200 to hold his/her breadth. As constituent elements of the electrocardiograph unit, a sound generator 16, an ECG sensor 17, and an ECG unit 18 are included.

The static-magnetic-field generating unit includes the magnet 1 and the static magnetic power supply 2. As the magnet 1, for example, a superconducting magnet or a normal magnet can be used. The static magnetic power supply supplies a current to the magnet 1. It is to be noted that the static magnetic power supply 2 is not required when a superconducting magnet is used as the magnet 1. Therefore, the static-magnetic-field generating unit generates a static magnetic field $B_0$ in a cylindrical aperture (an examination space) into which the subject 200 is moved. A magnetic field direction of this static magnetic field $B_0$ substantially coincides with an axial direction (a Z-axis direction) of the examination space. It is to be noted that the shim coil 14 is further provided to the static-magnetic-field generating unit. This shim coil 14 generates a correction magnetic field required to render a static magnetic field uniform based on current supply from the shim coil power supply 15 under control of the host computer 6.

The bed unit moves a top board on which the subject is laid down into or out of the examination space.

The gradient-magnetic-field generating unit includes the gradient coil unit 3 and the gradient power supply 4. The gradient coil unit 3 is arranged in the magnet 1. The gradient coil unit 3 includes three coils $3x$, $3y$, and $3z$ that generate respective gradient magnetic fields in an X-axis direction, a Y-axis direction, and a Z-axis direction orthogonal to teach other. The gradient power supply 4 supplies pulse currents required to produce gradient magnetic fields to the coils $3x$, $3y$, and $3z$ under control of the sequencer 5. Therefore, the gradient-magnetic-field generating unit synthesizes gradient magnetic fields in directions of the three axes (the X axis, the Y axis, and the Z axis) as physical axes by controlling the pulse currents fed to the coils $3x$, $3y$, and $3z$ from the gradient power supply 4 to arbitrarily set respective gradient magnetic fields in respective logical axis directions, i.e., a slice direction gradient magnetic field Gss, a phase encoding direction gradient magnetic field Gpe, and a read-out direction (frequency encoding direction) gradient magnetic field Gro which are orthogonal to each other. The respective gradient magnetic fields Gss, Gpe, and Gro in the slice direction, the phase encoding direction, and the read-out direction are superimposed on the static magnetic field $B_0$.

The transmitting/receiving unit includes the RF coil unit 7, the transmitter 8T, and the receiver 8R. The RF coil unit 7 is arranged near the subject 200 in the examination space. The transmitter 8T and the receiver 8R operate under control of the sequencer 5. The transmitter 8T supplies an RF current pulse of a Larmor frequency required to induce nuclear magnetic resonance (NMR) to the RF coil unit 7. The receiver 8R fetches an MR signal (a radio-frequency signal) such as an echo signal received by the RF coil unit 7, applies various kinds of signal processing, e.g., pre-amplification, intermediate-frequency conversion, phase detection, low-frequency amplification, or filtering to the fetched signal, and then performs analog-to-digital conversion to generate echo data (raw data) having a digital amount associated with the echo signal.

The control/computation unit includes the sequencer 5, the host computer 6, the computation unit 10, the storage unit 11, the display device 12, and the input device 13.

The sequencer 5 includes a CPU and a memory. The sequencer 5 stores pulse sequence information fed from the host computer 6 into the memory. The CPU of the sequencer 5 controls operations of the gradient power supply 4, the transmitter 8T, and the receiver 8R in accordance with the sequence information stored in the memory, temporarily inputs echo data output from the receiver 8R, and transmits this data to the computation unit 10. Here, the sequence information means all information required to operate the gradient power supply 4, the transmitter 8T, and the receiver 8R in accordance with a series of pulse sequence, and it includes information concerning, e.g., intensities, application times, and application timings of pulse currents applied to the coils $3x$, $3y$, and $3z$.

The host computer 6 has various kinds of functions realized by executing a preset software procedure. One of the functions is indicating the sequencer 5 pulse sequence information and collectively controlling operations of the entire apparatus. One of the functions is controlling the sequencer 5 to perform first imaging more than once while changing a central frequency of a fat suppression pulse. The first imaging is performed by using a phantom having a substantially uniform material as an imaging target. One of the functions is acquiring a frequency spectrum at a magnetic field central position and frequency spectrums at a plurality of positions other than the magnetic field central position based on a plurality of images obtained from the first imaging performed more than once. The spectrums have substantially the same distribution (waveform) but have a characteristic of shifting to be different from each other in a direction of a frequency axis. One of the functions is acquiring a shift amount in the direction of the frequency axis (hereinafter called "shift amount in the central frequncy" or more simply "shift amount") between the frequency spectrum at each of the plurality of positions and the frequency spectrum at the magnetic field central position. One of the functions is controlling the sequencer 5 to perform second imaging more than once by utilizing a pulse sequence in which a polarity of a gradient magnetic field in at least one direction is reversed from that in the above-explained pulse sequence while changing a central frequency of a fat suppression pulse. The second imaging is performed by using the phantom as an imaging target. One of the functions is acquiring a frequency spectrum at the magnetic field central position and a frequency spectrum at each of the plurality of positions other than the magnetic field central position based on a plurality of images obtained by the second imaging performed more than once. One of the functions is acquiring a shift amount in central frequency between the frequency spectrum at each of the plurality of positions where the frequency spectrums have been acquired based on the images obtained by the second imaging and the frequency spectrum at the magnetic field central position. One of the functions is calculating a shift amount of the central frequency that is dependent on a polarity of the gradient magnetic field and a shift amount of the central frequency that is not dependent on a polarity of the gradient magnetic field in regard to each of the plurality of positions based on the two shift amounts respectively obtained as explained above. One of the functions is detecting a minimum value of a signal intensity, a maximum value of the signal intensity, and a signal intensity of a part that is hardly affected by the fat suppression pulse in relation to each of the plurality of positions based on the plurality of images obtained by the first imaging performed more than once or the plurality of images obtained by the second imaging performed more than once. One of the functions is calculating a reduction amount of a fat suppression effect that is irrelevant to the frequency based on the minimum value, the maximum value, or the signal intensity detected in relation to each of the plurality of positions. One of the functions is comparing the shift amount of the central frequency that is dependent on the polarity of the gradient magnetic field, the shift mount of the central frequency that is not dependent on the polarity of the gradient magnetic field, and the reduction amount of the fat suppression effect that is irrelevant to the frequency with permissible levels preset in relation to these amounts, thereby determining acceptability based on comparison results. One of the functions is performing control so that all steps from the first imaging to determination of acceptability can be automatically continuously effected.

The computation unit 10 inputs echo data output from the receiver SR through the sequencer 5. The computation unit 10 arranges the input echo data in a Fourier space (which is also referred to as a k-space or a frequency space) set in an internal memory. The computation unit 10 subjects the echo data arranged in the Fourier space to two- or three-dimensional Fourier transformation to reconstruct image data of an actual space. Moreover, the computation unit 10 can execute, e.g., synthesis processing or difference calculation processing of data concerning an image as required.

The synthesis processing includes, e.g., addition processing of adding image data of a plurality of two-dimensional frames in accordance with each pixel, or maximum intensity projection (MIP) processing or minimum intensity projection (minIP) processing of selecting a maximum value or a minimum value in a visual line direction with respect to three-dimensional data. Additionally, as another example of the synthesis processing, axes of a plurality of frames may be aligned in a Fourier space to be synthesized as echo data into echo data of one frame. It is to be noted that the addition processing includes simple addition processing, addition-mean processing, weighted addition processing, and others.

The storage unit 11 stores reconstructed image data or image data subjected to the synthesis processing or the differential processing.

The display device 12 displays various kinds of images that should be presented to a user under control of the host computer 6. As the display device 12, a display device such as a liquid crystal display can be utilized.

The input device 13 inputs various kinds of information such as imaging conditions, information concerning a pulse sequence, image synthesis and differential calculation desired by an operator. The input device 13 transmits the input information to the host computer 6. The input device 13 appropriately includes a pointing device such as a mouse or a track ball, or a selection device such as a mode changeover switch, an input device such as a keyboard, and others.

The breath-holding instruction unit includes the sound generator 16. The sound generator 16 generates a message indicative of start of breath holding or end of breath holding in the form of sound in response to a command from the host computer 6.

The electrocardiograph unit includes the ECG sensor 17 and the ECG unit 18. The ECG sensor 17 is disposed to a surface of a body of the subject 200, and detects an ECG signal of the subject 200 as an electric signal (which will be referred to as a sensor signal hereinafter). The ECG unit 18 executes various kinds of processing including digitization processing to the sensor signal to be output to the sequencer 5 and the host computer 6. The sensor signal is used by the sequencer 5 when executing imaging scan. As a result, a synchronization timing based on an ECG gate method (an electrocardiographic synchronization method) can be appropriately set, and imaging scan of the ECG gate method based on this synchronization timing can be effected to collect data.

An operation of the MRI apparatus 100 having the above-described structure will now be explained hereinafter in detail.

The MRI apparatus 100 has a function of performing magnetic resonance imaging with respect to a subject by using various known imaging methods. The imaging method that can be used by such an MRI apparatus 100 includes a fat suppression method. However, an operation for this method is the same as that of a conventional MRI apparatus. The MRI apparatus 100 additionally has an operation mode where spatial inhomogeneity of a fat suppression effect in imaging utilizing the fat suppression method is analyzed (which will be referred to as an inhomogeneity analysis mode hereinafter). A characteristic operation of the MRI apparatus 100 is an operation in this inhomogeneity analysis mode. Therefore, an operation when the inhomogeneity analysis mode is set will now be explained hereinafter.

The inhomogeneity analysis mode is set by, e.g., an operator as part of a maintenance operation for the MRI apparatus 100. Further, at this time, in place of the subject 200, a phantom that has water or a fat component substantially uniformly put therein and a relatively uniform signal intensity is arranged in the examination space. It is desirable For this phantom to have a spherical shape or a cylindrical shape. Furthermore, contents of the phantom are, e.g., copper sulfate or baby oil.

Figure 2:
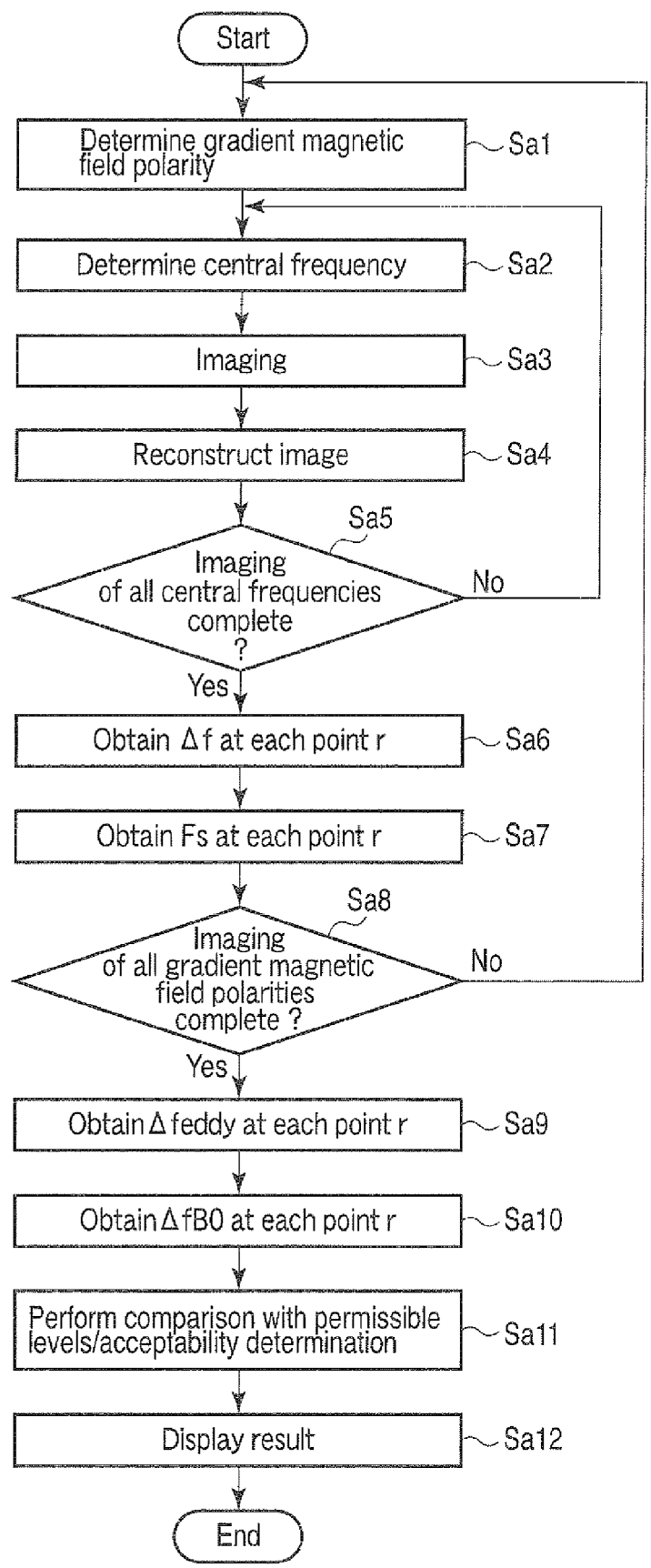
FIG. 2 is a flowchart showing a processing procedure of a host computer in FIG. 1 in an inhomogeneity analysis mode.

FIG. 2 is a flowchart showing a processing procedure of the host computer 6 in the inhomogeneity analysis mode.

In step Sa1, the host computer 6 sets a polarity of a gradient magnetic field to a predetermined initial polarity. Then, in step Sa2, the host computer 6 determines a central frequency of a fat suppression pulse as one of a plurality of candidate frequencies. It is desirable for the plurality of candidate frequencies to include a frequency at which a fat suppression effect does not occur at all in all pixels corresponding to regions where an imaging target is present to a frequency at which the fat suppression effect begins to disappear after a point where the fat suppression effect becomes maximum. However, frequencies in some bands alone in such frequency bands may be determined as candidate frequencies. The plurality of candidate frequencies are typically determined at even intervals. That is, assuming that n is the number of the candidate frequencies, the respective candidate frequencies are f0, df+f0, 2·df+f0, 3·df+f0 . . . , (n−1)·df+f0. However, the candidate frequencies may be provided at unequal intervals.

In step Sa3, the host computer 6 controls respective relevant units to perform imaging using the gradient magnetic field having the polarity determined in step Sa1 and the fat suppression pulse having the central frequency determined in step Sa2.

Figure 3:
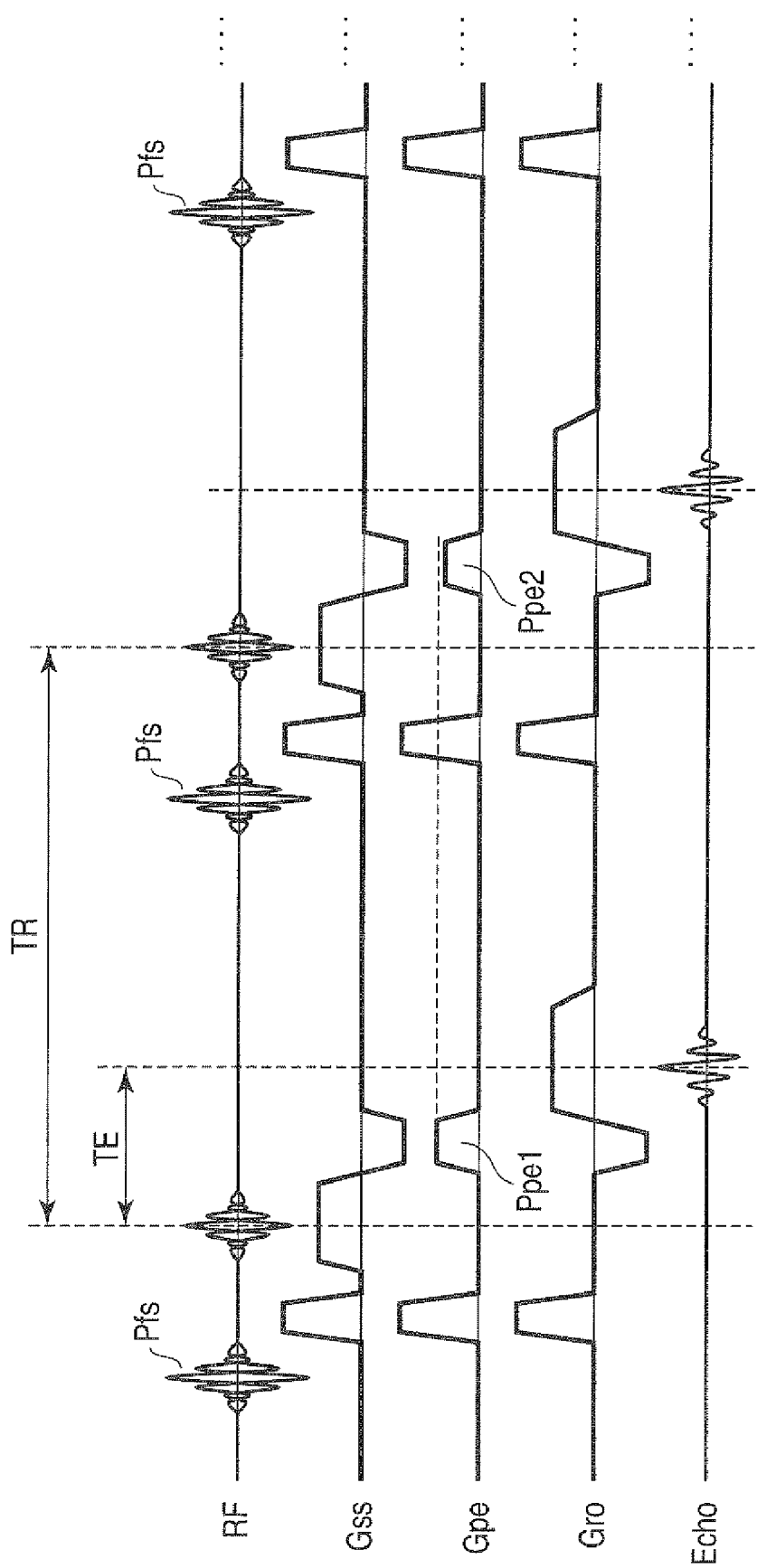
FIG. 3 is a view showing an example of a pulse sequence for imaging depicted in FIG. 2.

FIG. 3 is a view showing an example of a pulse sequence for imaging in step Sa3. In this pulse sequence, a CHESS method is used as a fat suppression method and a field echo method is utilized as an imaging method, respectively. TR denotes a repetition time, and TE designates an echo time. Phase encoding gradient pulses Ppe1, Ppe2, . . . for generation of a phase encoding direction gradient magnetic field Gpe are supplied to the gradient coil unit 3 from the gradient power supply 4 at the repetition time TR intervals. Areas of the phase encoding gradient pulses Ppe1, Ppe2, . . . are sequentially changed at fixed intervals. As a result, echo data subjected to phase encoding required for image reconstruction is sequentially collected.

In step Sa4, the host computer 6 instructs the computation unit 10 to reconstruct an image based on the echo data collected in step Sa3. In response to this instruction, the computation unit 10 arranges the collected echo data in a k-space to be subjected to Fourier transformation, thereby reconstructing the image. FIG. 4 is a view showing an example of the k-space. FIG. 5 is a view showing an example of the reconstructed image. It is to be noted that I(f,r) represents a signal value of a pixel at a position r (a vector) when f[Hz] represents a central frequency of a fat suppression pulse Pfs in the image depicted in FIG. 5.

In step Sa5, the host computer 6 confirms whether imaging with all the candidate frequencies determined as the central frequency has been completed. If there still remains a candidate frequency that is not determined as the central frequency, the host computer 6 repeats the processing in step Sa2 and the subsequent steps. This results in creation of a plurality of images taken while changing the central frequency of the fat suppression pulse Pfs. FIG. 6 is a conceptual illustration of the plurality of images created in this manner.

It is to be noted that, in the pulse sequence depicted in FIG. 3, two-dimensional imaging of one slice is performed, but two-dimensional multi-slice imaging or three-dimensional imaging is effected when obtaining a three-dimensional spatial dimension of the magnetic field.

If imaging with all the candidate frequencies determined as the central frequency has been completed by repeating steps Sa2 to Sa5 more than once, the host computer 6 advances to step Sa6 from step Sa5. In step Sa6, the host computer 6 obtains each shift amount $\Delta f$ of the central frequency in relation to a plurality of points in the images acquired in step Sa4. The points where the shift amounts $\Delta f$ are obtained may be determined as positions corresponding to all or arbitrary part of pixels in the images acquired in step Sa4.

A shift amount $\Delta f(r)$ at a given point r is obtained as follows. First, changes (frequency spectrums) in signal intensities (pixel values) in a frequency direction at a magnetic field center r0 and a position r are obtained, respectively. The frequency spectrums are obtained based on signal values at the magnetic field center r0 and the position r in the plurality of images acquired in step Sa4. As described above, the frequency spectrums at the respective positions have substantially the same distribution (waveform), but have a characteristic of shifting to be different in the frequency axis. Furthermore, these frequency spectrums are compared with each other to obtain the shift amount $\Delta f(r)$ of the central frequency at the position r.

FIG. 7 is a view showing an example of the frequency spectrums at the magnetic field center r0 and the position r. In FIG. 7, a broken line indicates the frequency spectrum at the magnetic field center r0 and a solid line indicates the frequency spectrum at the position r. As shown in FIG. 7, the shift amount $\Delta f(r)$ corresponds to a difference between frequencies at which signal values become minimum in both the frequency spectrums. It is to be noted that a generally known technique, e.g., a mutual correlation method or a cross-spectral method can be used to obtain this shift amount $\Delta f(r)$.

The shift amount $\Delta f(r)$ obtained here includes both a shift amount $\Delta feddy(r)$ of the central frequency caused due to a eddy magnetic field and a shift amount $\Delta fB0(r)$ of the central frequency caused due to magnetic field inhomogeneity. That is, $\Delta f(r)=\Delta feddy(r)+\Delta fB0(r)$ is achieved.

Figure 8:
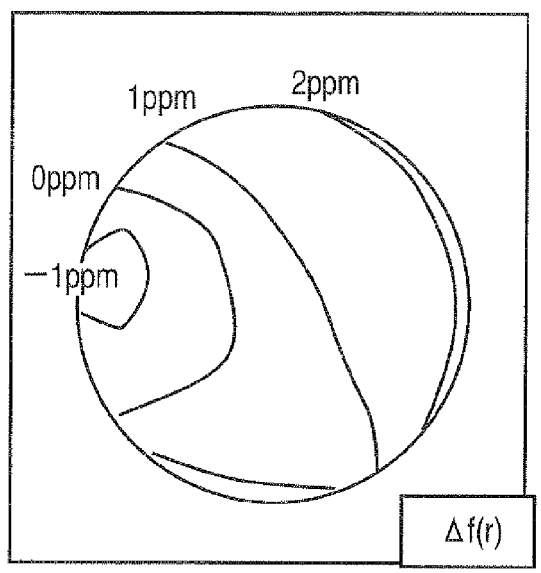
FIG. 8 is a view showing an example of an image obtained by arranging a plurality of shift amounts $\Delta f(r)$ in accordance with each position.

An aggregation of the shift amounts $\Delta f(r)$ obtained in relation to the plurality of points as explained above becomes data indicative of a distribution of the shift amounts of the central frequency. FIG. 8 is a view showing an example of an image obtained by arranging the plurality of shift amounts $\Delta f(r)$ acquired in step Sa6 in accordance with each position r.

In step Sa7, the host computer 6 obtains each of reduction amounts Fs of the fat suppression effect caused due to factors other than frequency shaft in relation to the plurality of points in the images acquired in step Sa4. The points where the reduction amounts Fs are obtained may be determined as positions corresponding to all or arbitrary part of pixels in the images acquired in step Sa4. It is general to set each point where the reduction amount Fs is obtained to be equal to each point where the shift amount $\Delta f$ is acquired. However, all or some of the points where the reduction amounts Fs are obtained may be set to positions different from the points where the shift amounts $\Delta f$ are acquired.

A reduction amount Fs(r) at the position r is obtained by the following expression based on a minimum value Imin(r) and a maximum value Imax(r) in respective signal values I(f,r) at the position r in the plurality of images acquired in step Sa4.

$$Fs(r)=1-\{Imin(r)/Imax(r)\}$$

Alternatively, the reduction amount Fs(r) may be obtained from the following expression based on a signal intensity Ins(r) at a frequency where the fat suppression pulse effect is not observed.

$$Fs(r)=1-\{Imin(r)/Ins(r)\}$$

It is to be noted that the minimum value Imin(r) may be substituted by a signal value I(fc,r) at a central frequency fc where a frequency spectrum become symmetrical.

Figure 9:
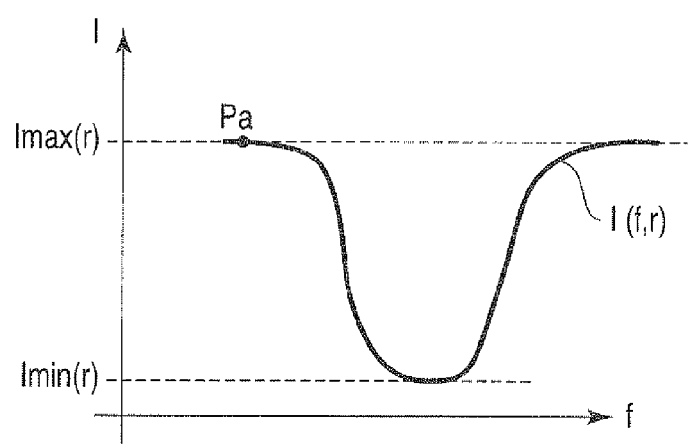
FIG. 9 is a view showing an example of a relationship between frequency spectrums obtained in regard to positions based on a plurality of images, a minimum value Imin(r), and a maximum value Imax(r)
Figure 10:
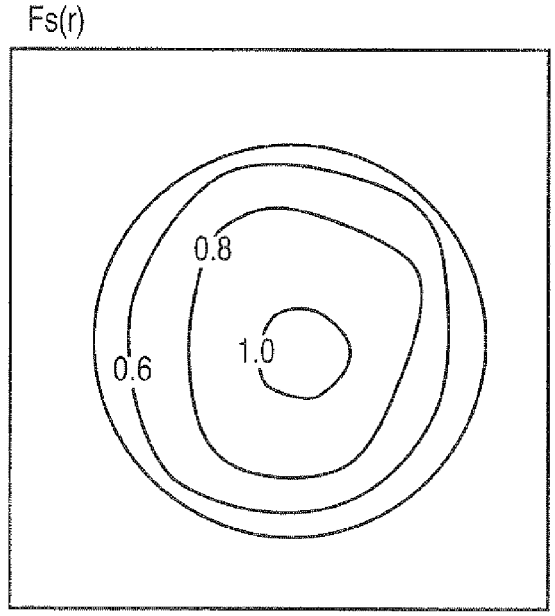
FIG. 10 is a view showing an example or an image obtained by arranging a plurality of reduction amounts Fs in accordance with each position.

FIG. 9 is a view showing an example of a relationship between the frequency spectrum, the minimum value Imin(r), the maximum value Imax(r), and Ins(r) obtained in relation to the position r based on the plurality of images acquired in step Sa4. FIG. 10 is a view showing an example of an image obtained by arranging the plurality of reduction amounts Fs acquired in step Sa7 in accordance with each position r.

Meanwhile, when a frequency of the fat suppression pulse sufficiently greatly deviates from a frequency difference between water and a fat tissue (e.g., if it deviates approximately 700 Hz in a 1.5 T apparatus), this can be regarded as conditions that signal suppression cannot be performed by using the fat suppression pulse even if an imaging target contains either water or fat. Thus, a signal intensity in this case is determined as Ins(r). This Ins(r) can be represented as a signal intensity at a point Pa in FIG. 9.

Figure 11:
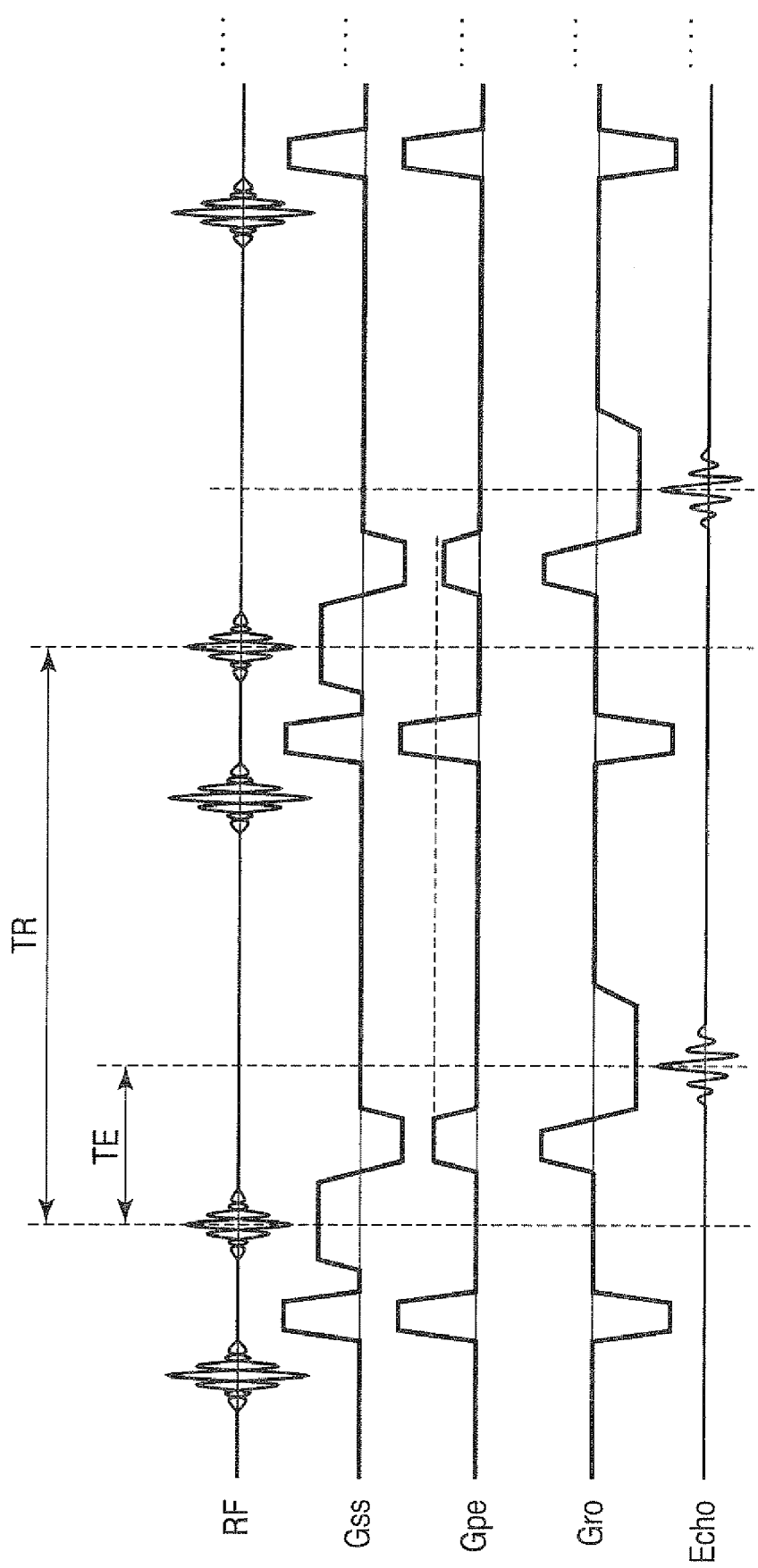
FIG. 11 is a view showing an example of a pulse sequence for imaging when a read-out direction gradient magnetic field is reversed.
Figure 12:
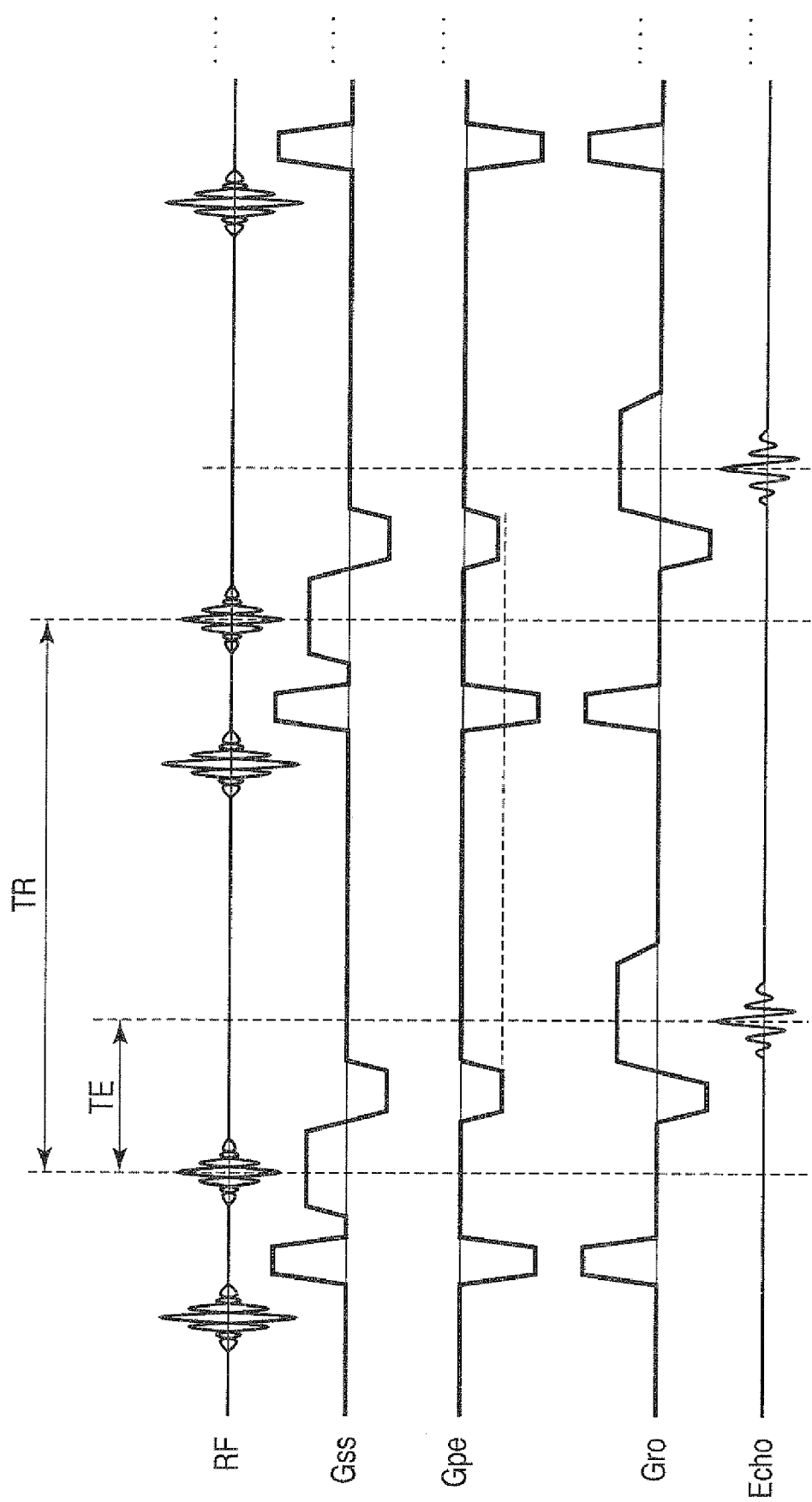
FIG. 12 is a view showing an example of a pulse sequence for imaging when a phase encoding gradient magnetic field is reversed.
Figure 13:
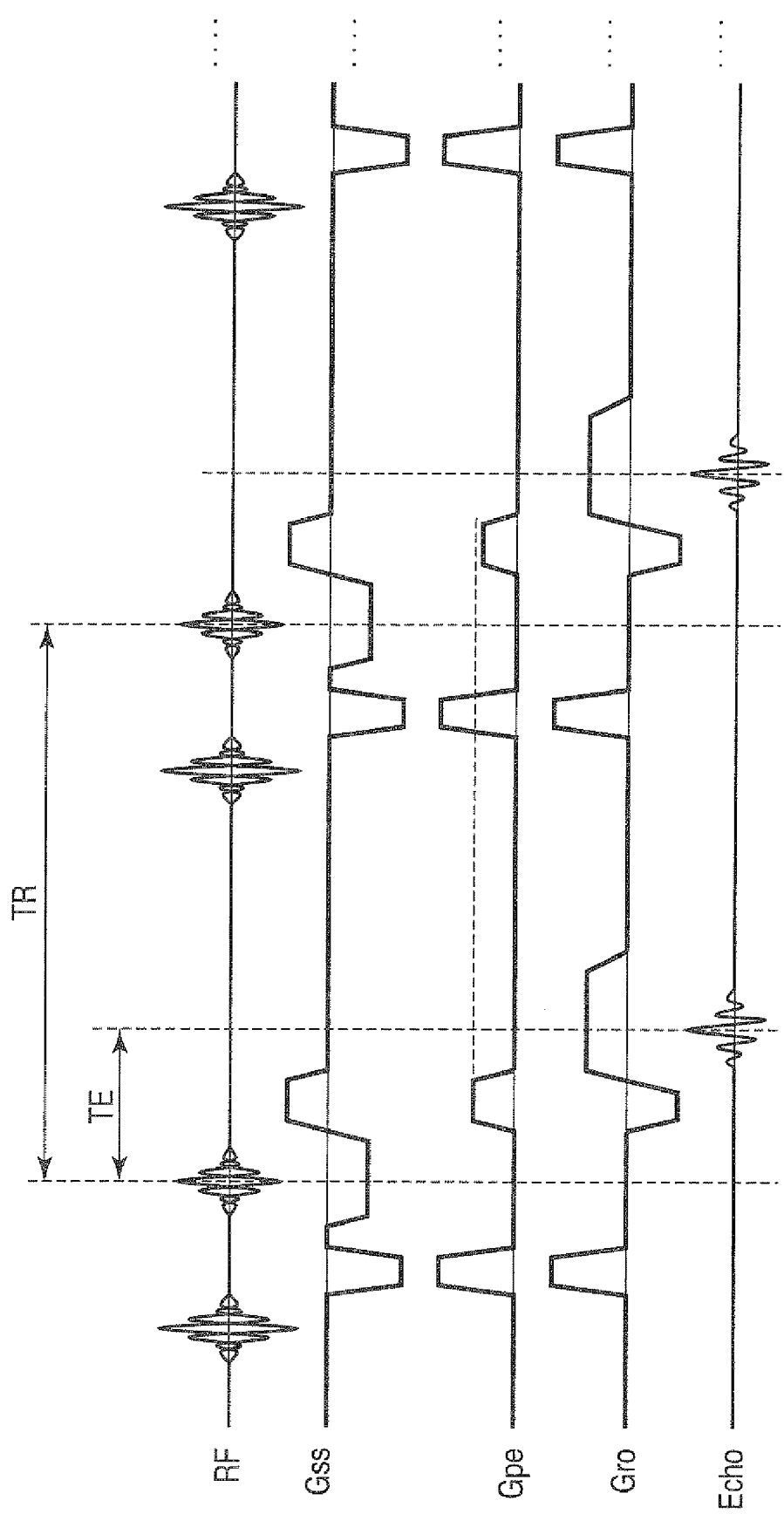
FIG. 13 is a view showing an example of a pulse sequence for imaging when a slice selective gradient magnetic field is reversed.

In step Sa8, the host computer 6 confirms whether imaging using all gradient magnetic field polarities has been completed. Moreover, if imaging using one gradient magnetic field polarity alone has been performed, the host computer 6 returns to step Sa1 from step Sa8. Additionally, the host computer 6 determines the gradient magnetic field polarity in such a manner that the polarity of the gradient magnetic field pulse in one direction alone is reversed from that determined at the previous step Sa1, and then again executes steps Sa2 to Sa5. It is to be noted that the gradient magnetic field polarity alone is changed in imaging in step Sa3 and any other conditions are the same as those in the previous time. The gradient magnetic field may be reversed in any channel depending on a purpose or reversal may be simultaneously carried out in all channels. FIG. 11 is a view showing an example of a pulse sequence for imaging in step Sa3 when a frequency read-out direction gradient magnetic field Is reversed. FIG. 12 is a view showing an example of a pulse sequence for imaging in step Sa3 when a phase encoding gradient magnetic field is reversed. FIG. 13 is a view showing an example of a pulse sequence for imaging in step Sa3 when a slice selective gradient magnetic field is reversed.

Figure 14:
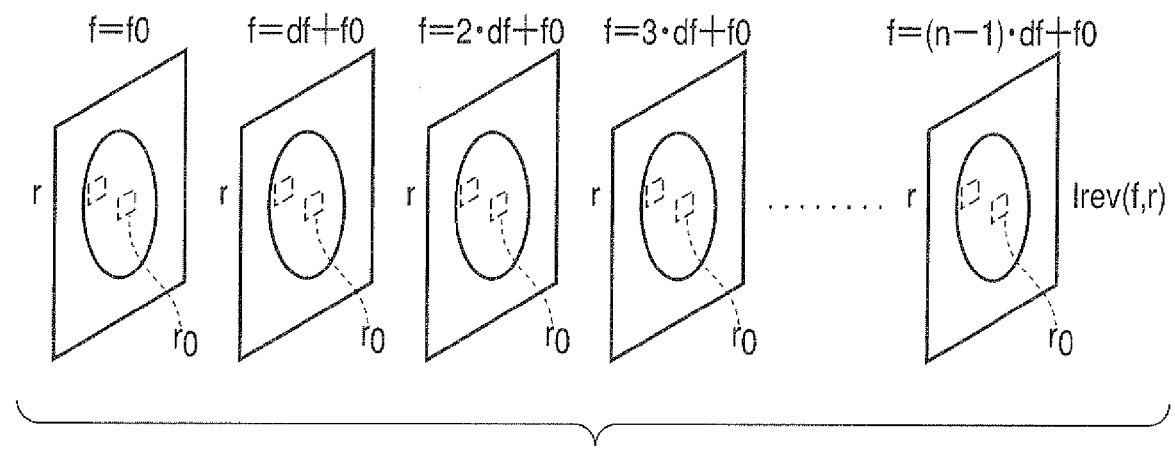
FIG. 14 is a view showing a conceptual illustration of images created by processing depicted in FIG. 2.

When steps Sa2 to Sa5 are repeated more than once, each central frequency of the fat suppression pulse Pfs is changed and a plurality of images taken with the reversed polarity of the gradient magnetic field pulse are created. FIG. 14 is a view showing a conceptual illustration of images created in this manner. Each signal value in the images obtained here is represented as Irev(f,r).

Figure 15:
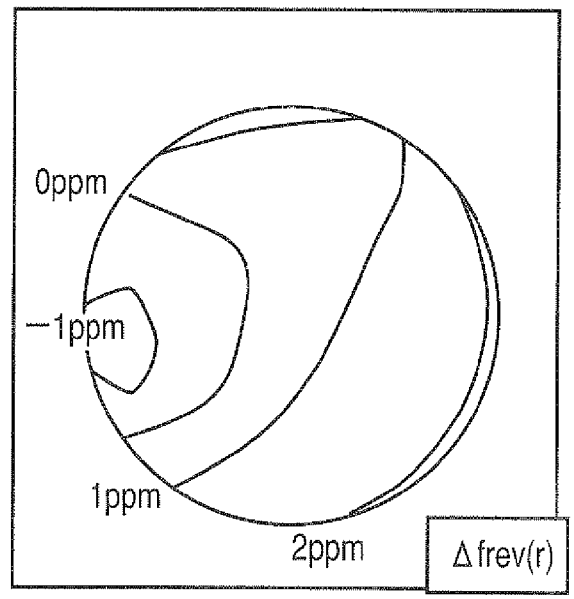
FIG. 15 is a view showing an example of an image obtained by arranging a plurality of shift amounts Δfrev(r) in accordance with each position.

Additionally, the host computer 6 obtains a shift amount $\Delta$frev(r) associated with the shift amount $\Delta$f(r) and a reduction amount Fsrev(r) associated with the reduction amount Fs(r) by executing steps Sa6 and Sa7 as in the above explanation with each image having the signal value Irev(f,r) determined as a target. It is to be noted that execution of step Sa7 may be omitted the second time. FIG. 15 is a view showing an example of an image obtained by arranging the plurality of shift amounts $\Delta$frev(r) acquired in step Sa6 in accordance with each position r. Target points where the reduction amounts Fs are obtained may be determined as positions corresponding to all or arbitrary part of pixels in the images acquired in step Sa4. Further, it is general to determine target points where the shift amounts $\Delta$frev(r) are obtained to be equal to the points where the shift amounts $\Delta$f are acquired. However, all or some of the target points where the shift amounts $\Delta$frev(r) are obtained may be determined as positions different from the points where the shift amounts $\Delta$f are acquired.

When imaging with reversal of the polarity of the gradient magnetic field pulse has been completed, the host computer 6 advances to step Sa9 from step Sa8. In steps Sa9 and Sa10, the host computer 6 obtains a shift amount $\Delta$feddy(r) and a shift amount $\Delta$fB0(r) in relation to each of the points where the shift amounts $\Delta$f(r) and the shift amounts $\Delta$Frev(r) are acquired based on the following expression. It is to be noted that the shift amount $\Delta$feddy(r) is a shift amount of the central frequency that is dependent on the polarity of the gradient magnetic field and the shift amount $\Delta$fB0(r) is a shift amount of the central frequency that is not dependent on the polarity of the gradient magnetic field.

$$\Delta feddy(r) = \{\Delta f(r) - \Delta frev(r)\}/2$$

$$\Delta fB0(r) = \{\Delta f(r) + \Delta frev(r)\}/2$$

It is general to set each target point where the shift amount $\Delta$feddy(r) or the shift amount $\Delta$fB0(r) is obtained to be equal to each target point where the shift amount $\Delta$f or the shift amount $\Delta$Frev(r) is acquired. However, all or some of the target points where the shift amounts $\Delta$feddy(r) or the shift amounts $\Delta$fB0(r) are obtained may be set to positions different from the target points where the shift amounts $\Delta$f or the shift amounts $\Delta$Frev(r) are acquired. Further, although it is general to set each target point where the shift amount $\Delta$feddy(r) and each target point where the shift amount $\Delta$fB0(r) is obtained to the same position, but all or some of these target points may be set to different positions.

When each shift amount $\Delta$frev concerning the same position as the shift amount $\Delta$f is not obtained, it is good enough to estimate the shift amount $\Delta$frev at this position from the shift amount $\Delta$frev acquired in relation to a neighboring position. Contrary, when each shift amount $\Delta$f concerning the same position as the shift amount $\Delta$frev is not obtained, it is good enough to estimate the shift amount $\Delta$F at this position from the shift amount $\Delta$f acquired in relation to a neighboring position. Furthermore, the shift amount $\Delta$f and the shift amount $\Delta$frev concerning a position where both the shift amount $\Delta$f and the shift amount $\Delta$frev are not acquired can be estimated from the shift amount $\Delta$f and the shift amount $\Delta$frev acquired in relation to a neighboring position.

Figure 16:
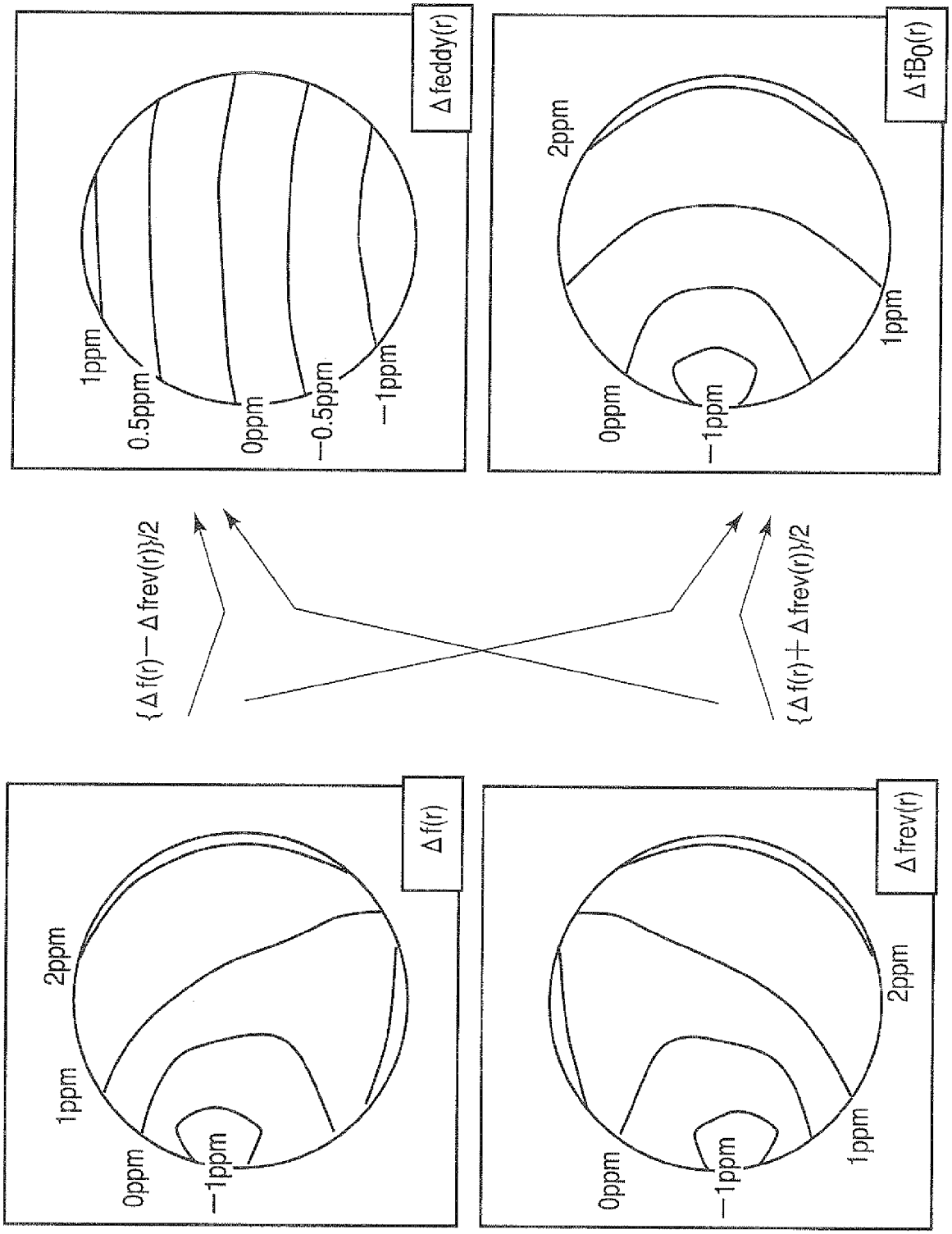
FIG. 16 is a schematic view of processing for obtaining a shift amount Δfeddy(r) and a shift amount ΔfB0(r).

FIG. 16 is a schematic view of processing for obtaining the shift amount $\Delta$feddy(r) and the shift amount $\Delta$fB0(r). This FIG. 16 also shows an example of images respectively obtained by arranging the shift amount $\Delta$feddy(r) and the shift amount $\Delta$fB0(r) in accordance with each position r.

In step Sa11, the host computer 6 compares the shift amount $\Delta$feddy(r), the shift amount $\Delta$fB0(r), and the reduction amount Fs(r) with permissible levels previously determined in relation to these amounts to determine acceptability of spatial evenness of the fat suppression effect. This acceptability determination is individually carried out with respect to spatial evenness of the fat suppression effect caused due to a eddy magnetic field, spatial evenness of the fat suppression effect caused due to magnetic field inhomogeneity, and spatial evenness of the fat suppression effect caused due to a reduction in the fat suppression effect based on a factor other than frequency shift. It is to be noted that, as the permissible levels, adopting, e.g., threshold values determined in accordance with each position r in relation to each of the shift amount $\Delta$feddy(r), the shift amount $\Delta$fB0(r), and the reduction amount Fs(r) is considered. Moreover, the shift amount $\Delta$feddy(r), the shift amount $\Delta$fB0(r), and the reduction amount Fs(r) are compared with their threshold values in accordance with each position r. The acceptability determination can be made by collating preset acceptability determination conditions with results of the above-explained comparison while considering performances required for the MRI apparatus 100.

In step Sa12, the host computer 6 displays a result of the acceptability determination in step Sa11 in the display device 12.

As explained above, according to this embodiment, respective spatial distributions of the shift amount Δfeddy(r) of the central frequency caused due to the eddy magnetic field, the shift amount ΔfB0(r) of the central frequency caused due to magnetic field inhomogeneity, and the reduction amount Fs(r) of the fat suppression effect due to a factor other than frequency shift are individually obtained. Additionally, acceptability determination of each of these amounts is performed, and a result is displayed. Therefore, even if spatial inhomogeneity of the fat suppression effect in images obtained by the MRI apparatus 100 becomes considerable, an operator can easily grasp which one of central frequency shift cue to a eddy magnetic field, central frequency shift due to magnetic field inhomogeneity, and a reduction in the fat suppression effect caused by a factor other than frequency shift is a cause of this spatial inhomogeneity. That is, cause unfolding of a problem that is difficult in the conventional technology can be readily performed. Therefore, an appropriate countermeasure (adjustment or component replacement) for a correct cause can be efficiently carried out. That is, even an inexperienced operator can take an appropriate countermeasure. Further, since all measurements and analyses are automated, labors of an operator (e.g., a fat suppression examiner or an adjustment operator) can be reduced.

Furthermore, since quality control can be performed in such a manner that spatial inhomogeneity of the fat suppression effect in each of the plurality of MRI apparatuses 100 can be set to a given fixed criterion or below, inhomogeneity of the fat suppression effect between the apparatuses can be reduced. As a result, performance comparison between the apparatuses can be facilitated, thereby improving a cost for coping with a problem and a difficulty level in relation to fat suppression by a maintenance operator.

This embodiment can be modified in many ways as follows.

(1) All or some of steps Sa6, 7, 8, 10, and 11 can be likewise performed in the computation unit 10 under control of the host computer 6.

(2) The reduction amount Fs may be obtained by using each of a maximum value of the signal value Irev (f,r), a minimum value of the signal value Irev(f,r), and a signal intensity of a part which is detected from the signal value Irev(f,r) and not subjected to fat suppression in place of the minimum value Imin(r), the maximum value Imax(r), and the signal intensity Ins(r). That is, the reduction amount Fs obtained based on the second taken images when step Sa7 is performed for the second time may be enabled. Therefore, in this case, the processing of obtaining the reduction amount Fs based on the first taken images in step Sa7 performed for the first time may be omitted.

(3) Each pixel whose image value (a signal value) is equal to or below a preset threshold value in each image which is additionally taken and not subjected to fat suppression or each image taken with a frequency at which Ins(r) is measured may be excluded from an acceptability determination target. As a result, a time required for the acceptability determination processing can be reduced, and a risk of misdetermination can be decreased. It is to be noted that a pixel that is relevant to the above-explained conditions corresponds to a position where a phantom is not present, and hence performing the acceptability determination is meaningless. Therefore, even if this pixel is excluded from the acceptability determination target, an accuracy for the acceptability determination is not reduced at all.

(4) In step Sa12, a countermeasure method for an item which is determined to be unacceptable in step Sa11 may be presented to an operator. For example, when the shift amount Δfeddy(r) is unacceptable, since the fat suppression effect can be improved by offsetting the gradient magnetic field or f0 at the time of application of the fat suppression pulse or the water excitation pulse to cancel out this shift amount Δfeddy (r), the operator is informed of this offset. Furthermore, when the reduction amount Fs(r) is unacceptable, since a failure or a defect of the RF coil, the RF amplifier, or any other component in the RF system or adjustment insufficiency of the pulse sequence can be detected by comparing a distribution of the reduction amount Fs(r) with the appropriately adjusted apparatus, the operator is informed of this detection.

(5) Information concerning the shift amount Δfeddy(r), the shift amount ΔfB0(r), and the reduction amount Fs(r) may be presented to the operator without performing step Sa11, and the acceptability determination may be carried out by the operator. When presenting the information concerning the shift amount Δfeddy(r), the shift amount ΔfB0(r), and the reduction amount Fs(r) to the operator, it is good enough to display a distribution image of the shift amount Δfeddy(r) and the shift amount ΔfB0(r) depicted in FIG. 16 or a distribution image of the reduction amount Fs(r) depicted in FIG. 10, for example.

(6) The fat suppression effect can be improved by changing a frequency of the fat suppression pulse or a gradient magnetic field at the time of application or the fat suppression pulse while considering the shift amount Δfeddy(r), the shift amount ΔfB0(r), and the reduction amount Fs(r) at a position of an imaged cross section.

(7) The present invention can be applied to not only fat suppression imaging as well as any other imaging that is affected by a spatial distribution of a radio-frequency magnetic field or a eddy magnetic field. For example, diffusion weighted imaging utilizing an echo planar method has a property that an image is distorted in the phase encoding direction due to inhomogeneity of a eddy magnetic field or a static magnetic field. The present invention can be applied for investigation of a cause and a countermeasure for such a distortion of an image.

(8) The above-explained embodiment can be carried out with respect to a subject other than a phantom, e.g., a human body determined as an imaging target.

(9) A signal intensity concerning one candidate frequency can be obtained by obtaining an echo in a sequence where a phase encoding gradient pulse is determined as zero and subjecting this echo to one-dimensional Fourier transformation. Additionally, plotting signal intensities obtained in relation to a plurality of candidate frequencies in this manner enables acquiring such a profile as shown in FIG. 7. When such a method is adopted, an imaging time in step Sa3 can be reduced. Further, since the imaging time can be reduced, a time required for the processing depicted in FIG. 2 can be decreased. Therefore, an efficiency of the operation can be improved. Furthermore, this is preferable when a human body is an imaging target.

(10) The present invention is predicated on a fact that the imaging target has a single resonant frequency. However, a human body has two resonant frequencies corresponding to a water or a fat. For this reason, when a human body is determined as an imaging target, it is desirable to suppress a fat signal by using a fat suppression method which is not influenced by the inhomogeneity of the magnetic field. As the fat suppression method used in this case, an short T1 inversion recovery (STIR) method can be adopted, for example. In the STIR method, an inversion recovery (IR) pulse is applied a fixed time (e.g., 180 ms) before an excitation pulse is applied.

(11) At least one of a profile of a signal value I(f,r) at an arbitrary position, a profile of a signal value Irev(f,r), and such a profile as depicted in FIG. 9 may be displayed in step Sa12. The arbitrary position at this time is typically a magnetic field center r0. Moreover, this display may be performed in addition to display in the foregoing embodiment, or this display alone may be carried out without effecting steps Sa6, 7, and 9 to 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus (MRI) comprising:
    an imaging unit which performs MR imaging more than once with respect to an imaging target while changing a central frequency of a fat suppression pulse sequence utilized in an MRI scan each time imaging is performed;
    a generation unit which generates a plurality of reconstructed MR images based on magnetic resonance signals obtained by MR imaging being performed more than once; and
    a calculation unit which calculates factor information, which contributes to spatial inhomogeneity of a fat suppression effect based on the plurality of reconstructed MR images, and storing or outputting said factor information.

2. The magnetic resonance imaging apparatus according to claim 1, wherein the calculation unit obtains information related to inhomogeneity of a static magnetic field and information indicative of the fat suppression effect, which has no relation to a frequency shift of a fat suppression spectrum as the factor information contributing to the spatial inhomogeneity of the fat suppression effect.

3. The magnetic resonance imaging apparatus according to claim 2, wherein the calculation unit calculates a shift amount between two frequency spectrums obtained at a magnetic field central position and a position other than the magnetic field central position based on the plurality of MR images as the information related to inhomogeneity of the static magnetic field.

4. The magnetic resonance imaging apparatus according to claim 1, wherein the MR imaging unit performs MR imaging more than once while changing a polarity of at least one of a slice selective gradient magnetic field, a frequency read-out gradient magnetic field, and a phase encoding gradient magnetic field, and the calculation unit calculates at least one of information related to eddy magnetic field and information related to inhomogeneity of a static magnetic field based on a plurality of MR images obtained by the gradient magnetic field having a changed polarity as the factor information which contributes to the spatial in homogeneity of the fat suppression effect.

5. The magnetic resonance imaging apparatus according to claim 1, wherein the calculation unit calculates information related to inhomogeneity of a radio-frequency pulse as the factor information which contributes to the spatial inhomogeneity of the fat suppression effect.

6. The magnetic resonance imaging apparatus according to claim 1, further comprising a display unit which generates and displays an image representing spatial inhomogeneity of the fat suppression effect in a contour pattern as the factor information which contributes to the spatial in homogeneity of the fat suppression effect.

7. The magnetic resonance imaging apparatus according to claim 1, further comprising a correction unit which corrects at least one of a central frequency of a fat suppression pulse at the time of actual imaging and a gradient magnetic field pulse at the time of application of the fat suppression pulse based on the factor information which contributes to the spatial inhomogeneity of the fat suppression effect.

8. The magnetic resonance imaging apparatus according to claim 1, wherein the imaging unit obtains an echo without performing phase encoding in each of said imaging processes, which is performed more than once, and the generation unit subjects the echo obtained in each of said imaging processes, which is performed more than once to a one-dimensional Fourier transformation in order to generate each of said the plurality of MR images.

9. The magnetic resonance imaging apparatus according to claim 1, wherein the imaging unit also uses a short T1 inversion recovery (STIR) method in order to carry out MR imaging more than once.

10. An analysis method of a fat suppression effect in magnetic resonance imaging, (MRI), said method comprising:
    performing MR imaging more than once with respect to an imaging target while changing a central frequency of a fat suppression pulse sequence utilized in an MRI scan each time imaging is performed;
    generating a plurality of reconstructed MR images based on MR signals obtained by MR imaging performed more than once; and
    calculating factor information, which contributes to spatial inhomogeneity of the fat suppression effect based on the plurality of reconstructed MR images, and storing or outputting said factor information.

* * * * *